United States Patent [19]

Matsumura, deceased et al.

[11] 4,426,381

[45] Jan. 17, 1984

[54] CARBOXYLIC ACID DERIVATIVES

[75] Inventors: Shingo Matsumura, deceased, late of Kyoto, by Rumiko Matsumura, legal representative; Masahiro Kise, Kyoto; Masakuni Ozaki, Joyo; Shinichi Tada, Omiyawata; Kenji Kazuno, Shiga; Hisao Watanabe, Kyoto; Katsutoshi Kunimoto, Shiga; Masami Tsuda, Kyoto, all of Japan

[73] Assignee: Nippon Shinyaku Co., Ltd., Kyoto, Japan

[21] Appl. No.: 348,184

[22] Filed: Feb. 12, 1982

[30] Foreign Application Priority Data

Feb. 18, 1981 [JP] Japan .................................. 56-23582

[51] Int. Cl.$^3$ ................. C07D 475/00; A61K 31/495

[52] U.S. Cl. .................................. 424/250; 544/361; 546/65; 546/94

[58] Field of Search ................. 544/361, 364; 424/250

[56] References Cited

U.S. PATENT DOCUMENTS 3,882,125  5/1975  Dohmori et al. ................... 544/361

*Primary Examiner*—Donald G. Daus
*Assistant Examiner*—S. A. Gibson
*Attorney, Agent, or Firm*—Jacobs & Jacobs

[57] ABSTRACT

Quinolinecarboxylic acid derivatives, such as compound 7-fluoro-8-(4-methyl-1-piperazinyl)-5-oxo-1,2-dihydro-5H-thiazolo(3,2-a)-quinoline-4-carboxylic acid, a pharmaceutical composition containing the same and methods of treatment of bacterial and fungal infections using the same.

14 Claims, No Drawings

CARBOXYLIC ACID DERIVATIVES

The present invention relates to novel substituted carboxylic acid derivatives having antibacterial activity and, more particularly, it relates to compounds represented by the following general formula (I) and pharmaceutically acceptable acid addition salts thereof,

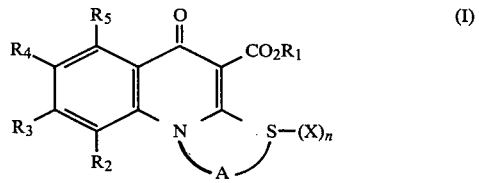

in which:

X is oxygen or nitrogen optionally substituted with alkyl, substituted phenyl or various acyl;

n is an integer of zero, one or two;

A is alkylene having one to five carbon atoms optionally substituted with substituent(s) selected from phenyl optionally substituted with lower alkyl or hydroxy, alkoxy, optionally substituted phenoxy, alkylthio, optionally substituted phenylthio, halogen, alkylamino, optionally substituted phenylamino, carboxy, nitro, cyano, carbonyl, thiocarbonyl and imino;

$R_1$ is hydrogen, alkali metal, e.g. lithium, sodium and potassium, alkaline earth metal, e.g. calcium, lower alkyl, pivaloyloxymethyl or phthalidyl;

$R_2$ is hydrogen or halogen;

$R_3$ is hydrogen, halogen, hydroxy, alkoxy or

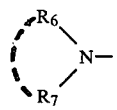

(in which $R_6$ and $R_7$ are the same or different and represent lower alkoxy or $R_6$ and $R_7$ form a five- to seven membered unsubstituted or substituted heterocyclic ring together with the nitrogen atom to which they are attached, which heterocyclic ring may contain other hetero atom(s), such as N, S and O, or $R_6$ and $R_7$ together form a salt);

$R_4$ is hydrogen, halogen, hydroxy or alkoxy;

$R_3$ and $R_4$ together with the carbon atoms to which they are attached form a ring containing only carbon and oxygen atoms; and $R_5$ is hydrogen, halogen, hydroxy, alkoxy or

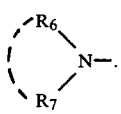

The terms "alkyl" and "alkoxy" mean alkyl and alkoxy of 1 to 10 carbon atoms, and the terms "lower alkyl" and "lower alkoxy" mean alkyl and alkoxy of 1 to 6 carbon atoms, preferably 1 to 4 carbon atoms, and most preferably 1 to 3 carbon atoms. Further, when $R_3$ and $R_4$ form a ring, they together preferably represent alkylenedioxy of 1 to 3 carbon atoms, most preferably methylenedioxy.

Examples of pharmaceutically acceptable salts of the compounds of the present invention are metal salts such as salts with lithium, sodium, potassium, and calcium; salts with organic bases such as ethanoldiamine and diethanolamine; salts with inorganic acids such as hydrochloric acid, sulfuric acid, and phosphoric acid; and salts with organic acids such as acetic acid, methanesulfonic acid, succinic acid, and lactic acid.

Nalidixic acid, piromidic acid or pipenidic acid have been widely used as synthetic antibacterials for diseases caused by Gram negative bacteria. Such compounds are not satisfactory for therapy of diseases caused by Gram positive bacteria and by Pseudomonas aeruginosa, which has been increasing in recent years. In order to solve the problem, various compounds have been synthesized and their antibacterial activity against many bacteria has been studied. As an improved antibacterial, the following compounds are now being developed: 6-halogeno-1-substituted-7-(4-substituted piperazino)-4-oxo-1, 4-dihydroquinoline-3-carboxylic acid derivatives (of Japanese Laid Open Patent Applications Sho-53-65887, 53-141286, 54-66686, 55-47658, and others); and the corresponding 6-fluoro-1,8-naphthylidine derivatives (Japanese Laid Open Patent Application Sho-55-83785).

Among synthetic antibacterials which were already known or which have been in a stage of development, there is no compound having substituents at the 2-position of a substituted quinoline carboxylic acid. In the literature, *Journal of Medicinal Chemistry*, volume 20, page 791, (1977), and volume 21, page 485, (1978), discloses compounds having methyl and hydroxy substituents but none of them exhibit appreciable antibacterial activity.

The antibacterial compounds of the present invention have a novel skeletal structure and they exhibit a strong antibacterial activity. The compounds of the invention are active against P. aeruginosa and are effective in small concentrations in the treatment of infections caused by both Gram positive and Gram negative bacteria. This is surprising, since antibacterial agents are generally apt to be effective against either Gram positive or Gram negative bacteria. Furthermore, to our surprise, the compounds are very strongly antibacterial against Eumycetes or true fungi. The compounds of the present invention can be safely used in therapy by oral administration to humans.

To prepare the compounds of the invention, it is useful to employ 4-oxo-1,4-dihydroquinoline-3-carboxylic acid ethyl ester (VII), as an intermediate. Intermediate (VII) can be synthesized by the following routes:

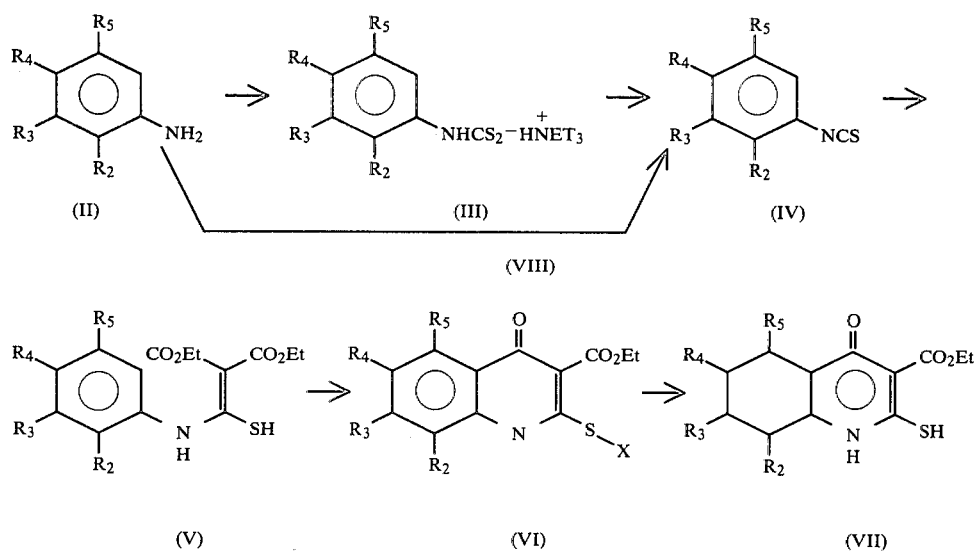

(V) (VI) (VII)

in which the meanings or $R_2$, $R_3$, $R_4$, and $R_5$ are the same as those given in the explanation for the compound (I), and Et is ethyl.

Thus, substituted aniline (II) is reacted with carbon disulfide with cooling in the presence or absence of adequate solvents, such as benzene, in the presence of an excess of triethylamine or various other amines and various alkali metals to provide a salt of substituted phenyl dithiocarbamic acid (III). This is then reacted with ethyl chlorocarbonate in such solvents as chloroform or methylene chloride in the presence of triethylamine or is reacted with cupper sulfate, lead nitrate, iron sulfate, zinc sulfate, and the like to afford the substituted phenyl isothiocyanate (IV). (IV) can also be directly manufactured from (II) by known methods (cf. Organic Synthesis, Collective Volume 1, page 447).

(IV) is then reacted with the sodium salt of diethyl malonate to give diethyl substituted phenyl aminomercaptomethylenemalonate (V). This is protected with a known thiol protective group, (see *The Chemistry of the Thiol Group*, Part two, Sal Patai, John Wiley and Sons, page 669, 1974) or with substituted alkyl by known methods to give (VI). Examples of useful and common protective groups, X, for the sulfur atom are substituted benzyl, alkoxymethyl, 2,4-dinitrophenyl, disulfide (as a dimer of the compound (V)), alkylthiomethyl, substituted carbamoyl, diphenylmethyl, triphenyl methyl, picolyl, acetamidomethyl, $\beta,\beta,\beta$-trifluoro-$\alpha$-acylaminoethyl, $\beta,\beta$-diethoxycarbonylethyl, acetyl, benzoyl, benzyloxycarbonyl, tetrahydropyranyl, benzylthiomethyl, phenylthiomethyl, isobutyroxymethyl, and the like. Taking substituted benzyl as an example, the reaction will be illustrated in some detail. Thus, p-methoxybenzyl chloride is made to react with the compound (V) in a solvent such as acetonitrile, dimethylformamide, tetrahydrofuran, and the like in the presence of an alkali such as sodium carbonate, potassium carbonate, and the like and the resulting compound is subjected to a cyclization by heating in high-boiling solvents such as dichlorobenzene, tetraline, diphenyl ether, diethylene glycol dimethyl ether, and the like to give the compound (VI) quantitatively.

The resulting (VI) is then subjected to a known adequate de-protection treatment to give the very important intermediate (VII) in good yield. For example, when the p-methoxybenzyl derivative of (VI) is used, the compound is treated with methanesulfonic acid, trifuloromethanesulfonic acid, trifluoroacetic acid, or a mixture thereof in the presence of anisole under cooling whereupon the protective group can be removed in good yield.

As shown below, the intermediate (VII) is, for example, reacted with a dihalide in the presence of potassium carbonate in dimethyl formamide solvent to afford compound (VIII) in which the nitrogen atom and sulfur atom of 2-mercaptoquinolone are contained in the same ring. Also, compound (VII) may be reacted with a halogeno substituted aldehyde, OHC—CH$_2$—B—Cl, where B is alkylene with zero to four carbon atoms unsubstituted or substituted by the same substituents as set forth for A to give (IX), in which there is an unsaturated bond in the same ring, as shown below.

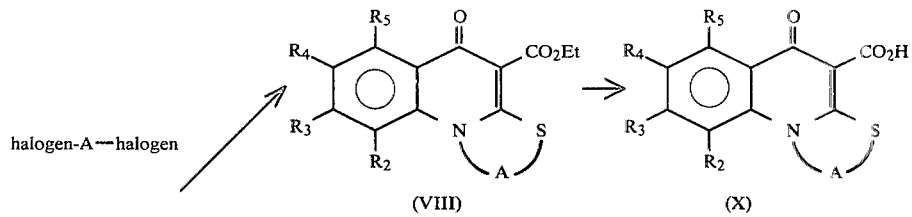

(VIII) (X)

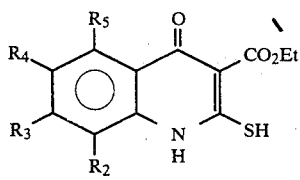

(VII)

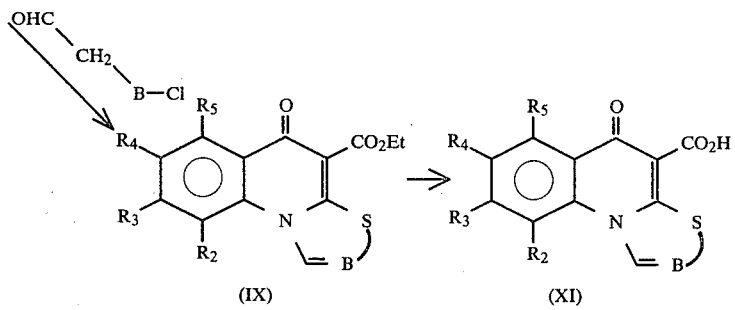

(IX) (XI)

The resulting (VIII) and (IX) are hydrolyzed in alcohol with sodium hydroxide, potassium hydroxide, and the like to give (X) and (XI), respectively, in good yields. When $R_3$ is halogen in (X) and (XI), such compounds can be subjected to a condensation with secondary amines represented by the formula (XII)

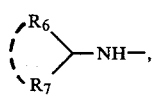

in which $R_6$ and $R_7$ are as defined above, to provide the compounds (XIII) and (XIV):

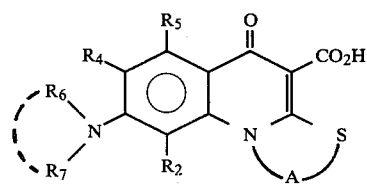
(XIII)

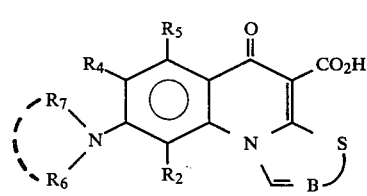
(XIV)

When $R_5$ is halogen in (X) and (XI), they may also be condensed with secondary amines of formula (XII) to provide compounds as in (XIII) and (XIV) but with

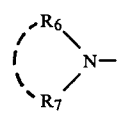

in place of $R_5$.

The free acid form of the compounds of the invention, such as (X) or (XIII), can be readily esterified or converted to the alkali metal or alkaline earth metal salt by known methods. The reaction schemes depicted above will thus produce compound (XV)

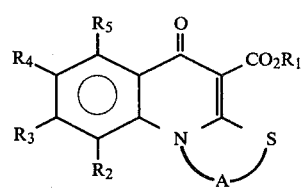
(XV)

which may be oxidized by known methods to give the corresponding sulfoxide and sulfone. Also, it may be changed to the corresponding sulfylimine and sulfoxyimine by known methods. Thus, the compound represented by the formula (I) and acid addition salts thereof can be manufactured in good yield in low cost.

Another synthetic route is as follows. Thus, the compounds (VIII) and (XVII) can be prepared starting from the compound (V) by the following way:

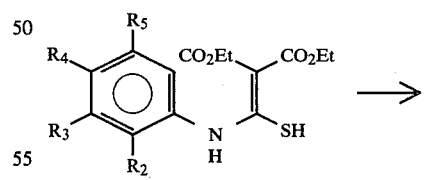
(V)

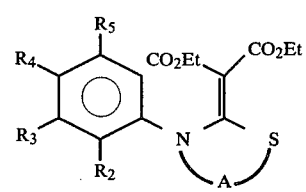
(XVI)

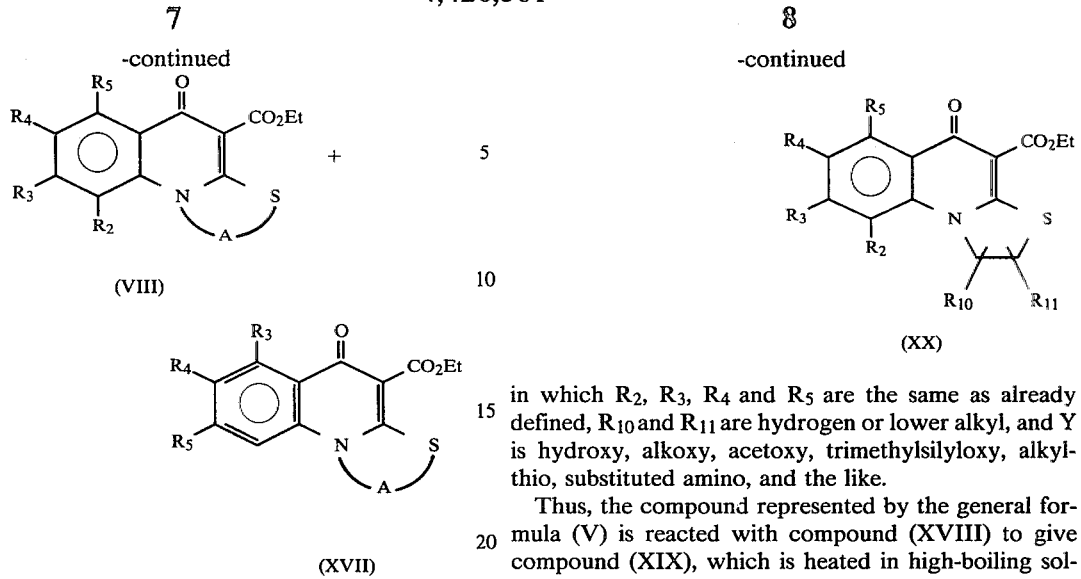

(VIII)

(XVII)

in which A, $R_2$, $R_3$, $R_4$ and $R_5$ are as already defined. Thus, compound (V) without a protective group for the sulfur atom, is reacted with halogen-A-halogen in dimethyl formamide solvent in the presence of potassium carbonate or is made to react with the halogeno substituted aldehyde previously described to give the compound (XVI). The resulting (XVI) is then subjected to a cyclization reaction by any known method, such as cyclization by heating or by the use of acidic substances, such as phosphorus oxychloride, phosphorus pentachloride, phosphorus trichloride, thionyl chloride, concentrated sulfuric acid, polyphosphoric acid, polyphosphoric acid esters, and the like. In carrying out the cyclization reaction using acidic substances, the acidic substance is used in an equimolar or an excess molar (preferably ten to twenty times molar) amount as compared to compound (XVI), and the mixture is generally heated at 100° to 150° C. for 0.5 to 2 hours. When $R_2$ is hydrogen in this case, the compound (XVII) in addition to (VIII) is produced as a cyclization product. Separation of (VIII) and (XVII) can be done by known method such as, for example, by recrystallization or by column chromatography.

When A is ethylene in the present invention compound (I), it can be prepared by the following route:

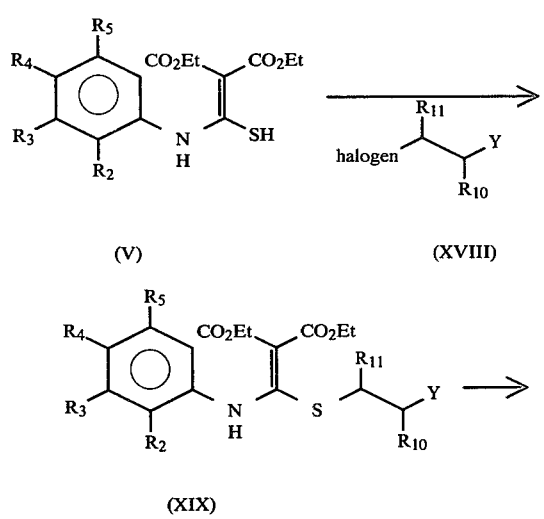

(XIX)

(XX)

in which $R_2$, $R_3$, $R_4$ and $R_5$ are the same as already defined, $R_{10}$ and $R_{11}$ are hydrogen or lower alkyl, and Y is hydroxy, alkoxy, acetoxy, trimethylsilyloxy, alkylthio, substituted amino, and the like.

Thus, the compound represented by the general formula (V) is reacted with compound (XVIII) to give compound (XIX), which is heated in high-boiling solvents, such as dichlorobenzene, tetraline, diphenyl ether, diethylene glycol dimethyl ether, and the like to give compound (XX) in high yield.

Example of Antibacterial Tests:

The following antibacterial tests were carried out according to a method of the Chemotherapeutic Society of Japan. Compounds obtained from Examples 7 and 9, which follow, illustrate the present invention. Gentamycin and 1-ethyl-6-fluoro-4-oxo-7-(1-piperazinyl)-1,4-dihydroquinoline-3-carboxylic acid, compound AM-715, are for comparison. The minimum inhibitory concentration of each compound for inhibiting growth of the specified organism is given in µg/ml.

TABLE I

|  | AM-715 | Gentamycin | Compd. of Ex. 7 | Compd. of Ex. 9 |
|---|---|---|---|---|
| Staphylococcus aureus 209P IC) | 0.19 | 0.1 | ≦0.19 | 0.19 |
| Staphylococcus aureus Smith | 0.39 | 0.19 | 0.19 | 0.19 |
| Staphylococcus aureus No. 41 | 0.39 | 0.39 | 0.19 | 0.19 |
| Streptococcus faecalis | 3.13 | 25 | 1.56 | 3.13 |
| List. monocytogenes RIMD1205030 | 3.13 | 0.78 | 1.56 | 1.56 |
| M. luteus ATCC 9341 | 12.5 | 1.56 | 12.5 | 6.25 |
| M. lysodeikticus | 6.25 | 0.19 | 1.56 | 6.25 |
| B. subtilis ATCC 6633 | 0.1 | ≦0.1 | 0.1 | 0.1 |
| E. coli NIHJ JC-2 | 0.1 | 3.13 | 0.1 | 0.39 |
| E. coli NIHJ | 0.05 | 1.56 | 0.05 | 0.1 |
| E. coli KC-14 | 0.05 | 3.13 | 0.05 | 0.1 |
| E. coli No. 29-3 | 0.025 | 3.13 | 0.05 | 0.05 |
| K. pneumoniae | 0.025 | 0.39 | 0.1 | 0.19 |
| K. sp. No. 18 | 0.1 | 3.13 | 0.19 | 0.39 |
| Se. marcescens IFO 3736 | 0.19 | 1.56 | 0.19 | 1.56 |
| Se. marcescens T-55 | 0.78 | 6.25 | 0.19 | 1.56 |
| Sal. typhymurium | 0.05 | 3.13 | 0.1 | 0.36 |
| P. vulgaris HX-19 | 0.05 | 1.56 | 0.025 | 0.025 |
| P. mirabilis 181 | 0.1 | 12.5 | 0.19 | 0.05 |
| Sh. flexneri | 0.025 | 3.13 | 0.05 | 0.11 |
| Ps. aeruginosa No. 12 | 0.78 | 0.78 | 1.56 | 3.13 |
| Ps. aeruginosa E-2 | 0.78 | 6.25 | 1.56 | 3.13 |
| Alc. faecalis | 6.25 | 6.25 | 1.56 | 3.13 |
| Aci. calcoaceticus 54 | 6.25 | 1.56 | 0.78 | 1.56 |

The Examples which follow illustrate the preparation of the Compounds according to the invention.

EXAMPLE 1

(1)

3-(4-Chlorophenyl)-1,3-thiazolidin-2-ylidene-malonic acid diethyl ester

Sodium hydride (purity: 50 percent) (5.7 grams) (0.118 mol) is suspended in 200 ml of dry dioxane and 18.9 g (0.118 mol) of diethyl malonate was dropped thereinto with stirring. The mixture was stirred at room temperature for thirty minutes and then 20.0 grams (0.118 mol) of 4-chlorophenyl isothiocyanate was dropped thereinto. The mixture was stirred for one hour, the content was concentrated in vacuo, the residue was washed with ether, and dried in vacuo to give 38.0 grams of sodium salt of diethyl 4-chloro-phenylaminomercaptomethylenemalonate, yellow powdery crystals.

The above sodium salt (5.0 grams; 0.014 mol) was dissolved in 15 ml of dimethyl formamide, 2.3 grams (0.017 mol) of anhydrous potassium carbonate was added thereto, 3.1 grams (0.017 mol) of ethylene dibromide was dropped thereinto at room temperature with stirring, the mixture was stirred at room temperature for overnight, the content was diluted with ice water, extracted with chloroform, and the residue was crystallized from ethyl acetate to give 4.4 grams (88.4 percent) of the title compound.

Elementary analysis calculated as $C_{16}H_{18}ClNO_4S$: C 54.01, H 51.0, N 3.44; Found: C 54.12, H 5.01, N 3.91.

Infrared absorption spectra (KBr, cm$^{-1}$): 1710, 1665, 1510, 1295.

Nuclear magnetic resonance spectra $\delta(CCl_4)$: 1.01 (6H, triplet, —CH$_2$CH$_3$ x 2), 3.10 (2H, triplet, C$_5$—H), 3.75 (4H, multiplet, —CH$_2$CH$_3$ x 2), 4.00 (2H, triplet, C$_4$—H), 6.90–7.40 (4H, multiplet, aromatic ring—H).

(2)

7-Chloro-5-oxo-1,2-dihydro-5H-thiazolo(3,2-a)quinoline-4-carboxylic acid 3-(4-Chlorophenyl)-1,3-thiazolidin-2-ylidenemalonic acid diethyl ester (2.76 grams; 7.8 mmol) was heated with stirring for 1.5 hours at 90° C. with 28 grams of polyphosphoric acid. After cooled, the content was poured into ice water, extracted with chloroform, washed with water, dried, and concentrated to give crystalline residue which was recrystallized from ethanol to give 1.65 grams (68.2 percent) of ethyl 7-chloro-5-oxo-1,2-dihydro-5H-thiazolo(3,2-a)quinoline-4-carboxylate. Melting point 321° C.

Elementary analysis calculated as $C_{14}H_{12}ClNO_3S$: C 54.28, H 3.90, N 4.52; Found: C 54.45, H 3.82, N 4.45

Infrared absorption spectra (KBr, cm$^{-1}$): 1700, 1670, 1590, 1480

Nuclear magnetic resonance spectra $\delta(CF_3CO_2S)$: 1.60 (3H, triplet, —CH$_2$CH$_3$), 3.86 (2H, triplet, C$_2$—H), 4.72 (2H, quartet, —CH$_2$CH$_3$), 5.22 (2H, triplet, C$_1$—H), 7.70–8.50 (3H, multiplet, aromatic ring—H).

The above compound (1.50 grams; 4.8 mmol) was suspended in a mixture of 3.0 grams of sodium hydroxide, 60 ml of ethanol and 40 ml of water, the mixture was heated to reflux for thirty minutes, acidified with acetic acid when the mixture was hot, the crystals separated were collected by filtration, washed with water, dried with air, and recrystallized from dimethyl formamide to give the title compound, 860 mg (63.2 percent), melting point 310° to 320° C. (decomposition).

Elementary analysis calculated as $C_{12}H_{18}ClNO_3S$: C 51.16, H 2.86, N 4.97; Found: C 51.32, H 2.69, N 4.97.

Infrared absorption spectra (KBr, cm$^{-1}$): 1695, 1590, 1480.

Nuclear magnetic resonance spectra $(CF_3CO_2D)$: 3.86 (2H, triplet, C$_2$—H), 5.25 (2H, triplet, C$_1$—H), 7.80 to 8.50 (3H, multiplet, aromatic ring—H).

EXAMPLE 2

7-Fluoro-5-oxo-1,2-dihydro-5H-thiazolo(3,2-a)quinoline-4-carboxylic acid

Diethyl 3-(5-fluorophenyl)-1,3-thiazolidin-2-ylidenemalonate (5.0 grams; 0.015 mol) was heated with 50.0 grams of polyphosphoric acid at 90° C. for 1.5 hours with stirring. After cooled, the content was poured into ice water, extracted with chloroform, washed with water, dried, and concentrated to give crystalline residue which was recrystallized from ethanol to give 1.9 grams (43.2 percent) of ethyl 7-fluoro-5-oxo-1,2-dihydro-5H-thiazolo(3,2-a)quinoline-4-carboxylate. Melting point: 225° to 226° C. Elementary analysis calculated as $C_{14}H_{12}FNO_3S$: C 57.33, H 4.12, N 4.78; Found: C 57.40, H 4.12, N 4.58.

Infrared absorption spectra (KBr, cm$^{-1}$): 1700, 1610, 1490, 1180.

Nuclear magnetic resonance spectra $\delta(CF_3CO_2D)$: 1.60 (3H, triplet —CH$_2$CH$_3$), 5.26 (2H, triplet, C$_1$—H), 3.87 (2H, triplet, C$_2$—H), 4.57 (quartet, —CH$_2$CH$_3$), 7.70 to 8.40 (3H, multiplet, aromatic ring—H).

The above compound (1.5 grams) (5.1 mmol) was suspended in a mixture of 3.0 grams of sodium hydroxide, 60 ml of ethanol and 40 ml of water, and the mixture was heated to reflux for thirty minutes. The mixture was acidified with acetic acid when it is still hot, the separated crystals were collected by filtration, washed with water, dried with air, and recrystallized from dimethyl formamide to give the title compound. The yield was 850 mg (63.0 percent). Melting point 315° to 325° C. (decomposition). Elementary analysis calculated as $C_{12}H_8FNO_3S$: C 54.33, H 3.04, N 5.28. Found: C 54.57, H 2.83, N 5.20.

Infrared absorption spectra (KBr, cm$^{-1}$): 1690, 1600, 1495, 1160.

Nuclear magnetic resonance spectra $\delta(CF_3CO_2D)$: 3.88 (2H, triplet, C$_2$—H), 5.29 (2H, triplet, C$_1$—H), 7.70 to 8.40 (3H, mult-iplet, aromatic ring—H).

EXAMPLE 3

7,8-Dichloro-5-oxo-1,2-dihydro-5H-thiazolo[3,2-a]quinoline-4-carboxylic acid

Diethyl 3-(3,4-dichlorophenyl)-1,3-thiazolidin-2-ylidenemalonate (5.7 grams, 0.015 mol) was heated with stirring for 1.5 hours at 90° C. with 32 grams of polyphosphoric acid, cooled, poured into ice water, the crystals separated out therefrom were collect-ed by filtration, washed with water, and air dried to give 4.2 grams (83.7 percent) of powdery crystals. This was a mixture of ethyl 7,8-dichloro-5-oxo-1,2-dihydro-5H-thiazolo[3,2-a]quinoline-4-carboxylate and ethyl 6,7-dichloro-5-oxo-1,2-dihydro-5H-thiazolo[3,2-a]quinoline-4-carboxylate. The mixture was recrystallized from dimethyl formamide twice to give 1.10 grams of ethyl 6,7-dichloro-5-oxo-1,2-dihydro-5H-thiazolo[3,2-a]quinoline-4-carboxylate. Melting point 266° to 267° C. Elementary analysis calculated as $C_{14}H_{11}Cl_2NO_3S$: C 48.85, H 3.22, N 4.07; Found: C 49.03, H 3.19, N 4.11.

Infrared absorption spectra (KBr, cm$^{-1}$): 1710, 1680, 1570, 1460.

Nuclear Magnetic resonance spectra δ(CF$_3$CO$_2$D): 1.60 (3H, triplet, —CH$_2$CH$_3$), 3.81 (2H, triplet, C$_2$—H), 4.73 (2H, quartet, —CH$_2$CH$_3$); 5.22 (2H, triplet, C$_1$—H), 7.73 (1H, doublet, C$_8$—H), 8.11 (1H, doublet, C$_9$—H).

A mixture (3.0 grams) recovered from the recrystallization mother liquor of the above compound was subjected to a column chromatography with 200 grams of silica gel (Wako Gel C-300, trademark) and chloroform to give 940 mg of ethyl 7,8-dichloro-5-oxo-1,2-dihydro-5H-thiazolo[3,2-a]quinoline-4-carboxylate. Melting point 255° to 257° C. Elementary analysis calculated as C$_{14}$H$_{11}$Cl$_2$NO$_3$S: C 48.85; H, 3.22, N 4.07; Found: C 48.97, H 3.21, N 3.96.

Infrared absorption spectra: (KBr, cm$^{-1}$) 1710, 1670, 1590, 1470, 1340, 1140

Nuclear magnetic resonance spectra δ(CF$_3$CO$_2$D): 1.60 (3H, triplet, —CH$_2$CH$_3$), 3.84 (2H, triplet, C$_2$—H), 4.70 (2H, quartet, —CH$_2$CH$_3$), 5.20 (2H, triplet, C$_1$—H), 8.00 (1H, singlet, C$_9$—H), 8.60 (1H, singlet, C$_6$—H).

The above compound (2.2 grams; 6.4 mmol) was suspended in a mixture of 4.0 grams of sodium hydroxide, 100 ml of ethanol and 100 ml of water and the mixture was heated to reflux for forty minutes. After cooled, it was acidified with acetic acid, the crystals separated out were collected by filtration, washed with water and dried to give 1.81 grams (89.6 percent) of the title compound. Melting point 305° to 315° C. (decomposition). Elementary analysis calculated as C$_{12}$H$_7$Cl$_2$NO$_3$S: C 45.59, H 2.23, N 4.43; Found: C 45.44; H 2.50, N 4.21.

Infrared absorption spectra (KBr, cm$^{-1}$): 1700, 1590, 1460, 1270.

Nuclear magnetic resonance δ(CF$_3$CO$_2$D): 3.81 (2H, triplet, C$_2$—H), 5.20 (2H, triplet, C$_1$—H), 7.99 (1H, singlet, C$_9$—H), 8.55 (1H, singlet, C$_6$—H).

EXAMPLE 4

6,7-Dichloro-5-oxo-1,2-dihydro-5H-thiazolo[3,2-a]quinoline-4-carboxylic acid

Ethyl 6,7-dichloro-5-oxo-1,2-dihydro-5H-thiazolo[3,2-a]quinoline-4-carboxylate (1.0 gram, 2.9 mmol) obtained in Example 3 was suspended in a mixture of 2.0 grams of sodium hydroxide, 140 ml of ethanol and 60 ml of water, the mixture was heated to reflux for thirty minutes, acidified with acetic acid when it was still hot, crystals separated out were collected by filtration, washed with water, and dried and recrystallized from dimethyl formamide to give 580 mg (62.8 percent) of the title compound. Melting point 305° to 310° C. (decomposition). Elementary analysis calculated as C$_{12}$H$_7$Cl$_2$NO$_3$S: C 45.59, H 2.23, N 4.43; Found: C 45.85, H 2.19, N 4.37.

Infrared absorption spectra (KBr, cm$^{-1}$): 1695, 1570, 1450, 1110.

Nuclear magnetic resonance spectra δ(CF$_3$CO$_2$D): 3.81 (2H, triplet, C$_2$—H), 5.20 (2H, triplet, C$_1$—H), 7.65 (1H, doublet, C$_8$—H), 8.08 (1H, doublet, C$_9$—H).

EXAMPLE 5

7-Chloro-6-(1-piperazinyl)-5-oxo-1,2-dihydro-5H-thiazolo[3,2-a]-quinoline-4-carboxylic acid A mixture of 500 mg (1.58 mmol) of 6,7-dichloro-5-oxo-1,2-dihydro-5H-thiazolo(3,2-a)quinoline-4-carboxylic acid, 1.0 gram (11.6 mmol) of piperazine, and 20 ml of pyridine was heated to reflux for ten hours. The content was then concentrated under reduced pressure, water was added to the residue, insoluble matters were taken out by filtration, washed with water, dried, and recrystallized from dimethyl formamide to give the title compound. Yield was 420 mg (72.7 percent). Melting point: 244° to 245° C. (decomposition). Elementary analysis calculated as C$_{16}$H$_{16}$ClN$_3$O$_3$S.2½ H$_2$O: C 46.77, H 5.15, N 10.22; Found: C 46.66, H 4.90, N 9.81.

Infrared absorption spectra (KBr, cm$^{-1}$): 1690, 1610, 1575, 1450, 1360.

Nuclear magnetic resonance spectra δ(CF$_3$CO$_2$D): 3.40-4.60 (8H, multiplet,

4.70-5.50 (4H, multiplet, C$_1$—H, C$_2$—H), 7.80-8.20 (2H, multiplet, aromatic ring—H).

EXAMPLE 6

8-Bromo-7-fluoro-5-oxo-1,2-dihydro-5H-thiazolo(3,2-a)-quinoline-4-carboxylic acid Diethyl 3-(3-bromo-4-fluorophenyl)-1,3-thiazolydin-2-ylidene-malonate (6.0 grams, 0.0143 mmol) was heated with stirring at 90° C. in 60 grams of polyphosphoric acid. After three hours, the content was poured over into ice water, the crystals separated out were collected by filtration, washed with water, and air dried. Then 5.14 grams (97%) of mixture of ethyl 8-bromo-7-fluoro-5-oxo-1,2-dihydro-5H-thiazolo(3,2-a)-quinoline-4-carboxylate and 6-bromo-7-fluoro-5-oxo-1,2-dihydro-5H-thiazolo(3,2-a) quinoline-4-carboxylic acid ethyl ester was obtained.

The above mixture (4.65 grams) was subjected to a column chromatography on 500 grams of silica gel using chloroform as a developer and from the distillate in initial stage, 1.41 grams of ethyl 8-bromo-7-fluoro-5-oxo-1,2-dihydro-5H-thiazolo(3,2-a)-quinoline-4-carboxylate was obtained. Melting point was 258° to 262° C. Elementary analysis calculated as C$_{14}$H$_{11}$BrFNO$_3$S: C 45.18, H 2.98, N 3.76; Found: C 45.32, H. 298, N 3.27.

Infrared absorption spectra (KBr, cm$^{-1}$): 1705, 1675, 1600, 1480.

Nuclear magnetic resonance spectra δ(CF$_3$CO$_2$D): 1.50 (3H. triplet, —CH$_2$CH$_3$), 3.82 (2H, triplet, C$_2$—H), 4.68 (2H, quartet, —CH$_2$CH$_3$), 5.20 (2H, triplet, C$_1$—H), 8.00-8.40 (2H, multiplet, aromatic ring—H).

Then ethyl 6-bromo-7-fluoro-5-oxo-1,2-dihydro-5H-thiazolo(3,2-a) quinoline-4-carboxylate was distilled out. This was recrystallized from dimethyl formamide. Melting point was 267° C. (decomposition). Elementary analysis calculated as C$_{14}$H$_{11}$BrFNO$_2$S: C 45.18, H 2.98, N 3.76; Found: C 45.19, H 3.02, N 3.71.

Infrared absorption spectra (KBr, cm$^{-1}$): 1710, 1675, 1620, 1470.

Nuclear magnetic resonance spectra δ(CF$_3$CO$_2$D): 1.60 (3H, triplet, —CH$_2$CH$_3$), 3.70 (2H, triplet, C$_2$—H), 4.71 (2H, quartet, —CH$_2$CH$_3$), 5.22 (2H, triplet, C$_1$—H), 7.70-8.00 (2H, multiplet, aromatic ring—H).

Then 1.0 gram of the fractioned ethyl 8-bromo-7-fluoro-5-oxo-1,2-dihydro-5H-thiazolo(3,2-a)-quinoline-4-carboxylate was suspended in a solution of 2.0 grams of sodium hydroxide (0.05 mmol), 50 ml of water and 20 ml of ethanol, the mixture was heated to reflux for four hours, the transparent solution was acidified with acetic acid after being cooled, crystals separated out were collected by filtration, washed with water, and dried. Thus, 860 mg (93.5 percent) of the title compound was obtained. Colorless powdery crystals were then recrystallized from dimethyl formamide. Melting point was 228° to 290° C. (decomposition).

Elementary analysis calculated as $C_{12}H_7BrFNO_3S$: C 41.88, H 2.05, N 4.07; Found: C 42.19, H 2.02, N 4.06.

Infrared absorption spectra (KBr, cm$^{-1}$): 1695, 190, 1470.

Nuclear magnetic resonance spectra $\delta(CF_3CO_2D)$: 3.80 (2H, triplet, $C_2$—H), 5.16 (2H, triplet, $C_1$—H), 7.70–8.30 (2H, multiplet, aromatic ring—H).

EXAMPLE 7

7-Fluoro-8-(4-methyl-1-piperazinyl)-5-oxo-1,2-dihydro-5H-thiazolo (3,2-a)-quinoline-4-carboxylic acid A mixture of 500 mg (1.45 mmol) of 8-bromo-7-fluoro-5-oxo-1,2-dihydro-5H-thiazolo(3,2-a) quinoline-4-carboxylic acid, 730 mg (7.25 mmol) of N-methylpiperazine and 10 ml of pyridine was heated to reflux for twelve hours on an oil bath. The conent was then concentrated under reduced pressure, water was added to the residue, insoluble matters were collected by filtration, washed with water, dried, and the resulting powder was recrystallized from dimethyl formamide to give 116 mg (22.0 percent) of the title compound. Melting point was 267° to 271° C. (decomposition).

Elementary analysis calculated as $C_{17}H_{18}FN_3O_3S$: C 56.19, H 4.99, N 11.56; Found: C 55.81, H 4.67, N 11.28.

Infrared absorption spectra (KBr, cm$^{-1}$): 1695, 1625, 1590.

Nuclear magnetic resonance spectra $\delta(CF_3CO_2D)$: 3.19 (3H, singlet, —NCH$_3$), 3.35–4.50 (10H, multiplet,

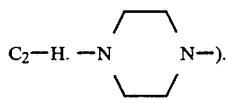

$C_2$—H. —N     N—).

5.18 (2H, triplet, $C_1$—H), 7.18 (1H, singlet, $C_9$—H), 8.12 (1H, doublet, $C_6$—H).

EXAMPLE 8

8-Bromo-7-fluoro-1-methyl-5-oxo-1,2-dihydro-5H-thiazolo(3,2-a) quinoline-4-carboxylic acid Diethyl 3-(3-bromo-4-fluorophenyl)-4-methyl-1,3-thiazolidin-2-ylidenemalonate (4.2 grams) was dissolved in 40 grams of polyphosphoric acid and the solution was heated with stirring at 90° C. for three hours. After the reaction, the content was poured over into ice water and extracted with chloroform to give 3.5 grams of sirupy substance. This was subjected to a column chromatography on 350 grams of silica gel using chloroform as a developer and, from the initial distillate, 620 mg of ethyl 8-bromo-7-fluoro-1-methyl-5-oxo-1,2-dihydro-5H-thiazolo(3,2-a) quinoline 4-carboxylate was obtained, Melting point was 211° C.

Elementary analysis calculated as $C_{15}H_{13}BrFNO_3S$: C 46.65, N 3.39, N 3.63; Found: C 46.59, H 3.28, N 3.57.

Infrared absorption spectra (KBr, cm$^{-1}$): 1720, 1670, 1640, 1605.

Nuclear magnetic resonance $\delta(CDCl_3)$: 1.40 (3H, triplet, —CH$_2$CH$_3$), 1.48 (3H, doublet, $C_1$—CH$_3$), 2.93 (1H, doublet, $C_2$—H), 3.61 (1H, doublet doublet, $C_2$—H), 4.32 (2H, quartet, —CH$_2$CH$_3$), 5.29 (1H, multiplet, $C_1$—H), 7.44 (1H, triplet, $C_9$—H), 7.94 (1H, doublet $C_6$—H).

Then 450 mg of ethyl 6-bromo-7-fluoro-1-methyl-5-oxo-1,2-dihydro-2H-thiazolo(3,2-a)-quinoline-4-carboxylate was obtained from the succeeding distillate. Melting point was 219° C.

Elementary analysis calculated as $C_{15}H_{13}BrFNO_3S$: C 46.65, H 3.39, N 3.63; Found: C 46.74, H 3.31, N 3.51.

Infrared absorption spectra (KBr, cm$^{-1}$): 1680, 1620, 1470.

Nuclear magnetic resonance spectra $\delta(CF_3CO_2D)$: 1.60 (3H, triplet, —CH$_2$CH$_3$), 1.65 (3H, doublet, $C_1$—CH$_3$), 3.36 (1H, doublet, $C_2$—H), 3.98 (1H, doublet, doublet, $C_2$—H), 4.70 (2H, quartet, —CH$_2$CH$_3$), 5.94 (1H, multiplet, $C_1$—H), 7.70–8.10 (2H, multiplet, aromatic ring—H).

Then 600 mg (1.55 mmol) of ethyl 8-bromo-7-fluoro-1-methyl-5-oxo-1,2-dihydro-5H-thiazolo(3,2-a)quinoline-4-carboxylate separated by column chromatography was suspended in 50 ml of ethanol containing 1.2 grams (0.02 mol) of potassium hydroxide and the mixture was heated to reflux for 1.5 hours. The content was concentrated under reduced pressure and, after water was added to the residue, insoluble matters were filtered and removed. This was acidified with acetic acid and crystals separated therefrom were collected by filtration, washed with water and dried to give 520 mg (93.7 percent) of the title compound. Recrystallized from dimethyl formamide. Melting point 290° to 291° C. (decomposition). Elementary analysis calculated as $C_{13}H_9BrFNO_3S$: C 43.59, H 2.53, N 3.91; Found: C 43.78, H 2.55, N 3.93.

Infrared absorption spectra (KBr, cm$^{-1}$): 1659, 1590, 1470.

Nuclear magnetic resonance spectra $\delta(CF_3CO_2D)$: 1.70 (3H, doublet, $C_1$—CH$_3$), 3.20–4.30 (2H, multiplet, $C_2$—H), 5.60–6.20 (1H, multiplet, $C_1$—H), 7.70–8.70 (2H, multiplet, aromatic ring—H).

EXAMPLE 9

7-Fluoro-1-methyl-8-(4-methyl-1-pierazinyl)-5-oxo-1,2-dihydro-5H-thiazolo(3,2-a)-quinoline-4-carboxylic acid A mixture of 400 mg (1.12 mmol) of 8-bromo-7-fluoro-1-methyl-5-oxo-1,2-dihydro-5H-thiazolo(3,2-a)-quinoline-4-carboxylic acid, 1.1 grams (1.12 mmol) of N-methylpiperazine and 20 ml of pyridine was heated to reflux for forty eight hours in an oil bath. When the reaction was completed, the content was concentrated in vacuo, then water was added to the residue, insoluble matter was collected by filtration, washed with water and dried to give 240 mg of the title compound. Recrystallized from dimethyl formamide. Melting point was 292° to 294° C. (decomposition). Elementary analysis calculated as $C_{18}H_{20}FN_3O_3S$: C 57.28, H 5.34, N 11.13; C 57.03, H 5.25, N 10.87.

Infrared absorption spectra (KBr, cm$^{-1}$): 1700, 1630, 1480.

Nuclear magnetic resonance spectra $\delta(CF_3CO_2D)$: 1.70 (3H, doublet, $C_1$—CH$_3$), 3.15 (3H, singlet, —NCH$_3$), 3.30–4.50 (10H, multiplet,

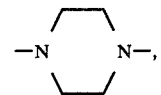

—N     N—, $C_2$—H), 5.60–6.20 (1H, multiplet, $C_1$—H), 7.20 (1H, wide singlet, $C_9$—H), 8.11 (1H, doublet, $C_6$—H).

EXAMPLE 10

Ethyl 7,8-methylenedioxy-5-oxo-1,2-dihydro-5H-thiazolo(3,2-a)quinoline-4-caroboxylate Diethyl 3-(3,4-methylenedioxyphenyl)-1,3-thiazolidin-2-ylidene malonate (5.37 grams, 0.015 mol) was heated with stirring in 50.0 grams of polyphosphoric acid at 80° to 90° C. and, after 1.5 hours, the content was poured over into ice water, insoluble matter was extracted with chloroform, washed with water, dried, concentrated, and the residue was recrystallized from dimethyl formamide to give 1.45 grams (30.9 percent) of the title compound, melting point 308° C. (decomposition). Elementary analysis calculated as $C_{15}H_{13}NO_2S$: C 56.42, H 4.10, N 4.39; Found: C 56.00, H 4.04, N 4.21.

Infrared absorption spectra (KBr, cm$^{-1}$): 1660, 1625, 1585, 1230, 1030.

Nuclear magnetic resonance specrra $\delta(CF_3CO_2D)$: 1.60 (3H, triplet, —CH$_2$CH$_3$), 3.78 (2H, triplet, $C_2$—H), 4.70 (2H, quartet, —CH$_2$CH$_3$), 5.10 (2H, triplet, $C_1$—H), 6.25 (2H, singlet, O—CH$_2$—O), 7.14 (1H, singlet, $C_9$—H), 7.70 (1H, singlet, $C_6$—H).

EXMPLE 11

7,8-Methylenedioxy-5-oxo-1,2-dihydro-5H-thiazolo(3,2-a)-quinoline-4-carboxylic acid Ethyl 7,8-methylenedioxy-5-oxo-1,2-dihydro-5H-thiazolo(3,2-a) quinoline-4-carboxylate (1.38 grams, 4.3 mmol) was suspended in a mixture of 2.0 grams of sodium hydroxide, 40 ml of ethanol and 30 ml of water and the whole mixture was heated to reflux for thirty minutes. Then it was acidified with acetic acid when the solution was still hot, the crystals separated out were collected by filtration, washed with water and air dried and the resulting crude crystals were recrystallized from dimethyl formamide to give 870 mg (69.0 percent) of the title compound, melting point 315° to 320° C. (decomposition). Elementary analysis calculated as $C_{13}H_9NO_5S$: C 53.61, H 3.11, N 4.81; Found: C 53.68, H 2.92, N 4.66.

Infrared absorption spectra (KBr, cm$^{-1}$): 1695, 1630, 1270, 1040.

Nuclear magnetic resonance spectra $\delta(CF_3CO_2D)$: 3.80 (2H, triplet, $C_2$—H), 5.15 (2H, triplet, $C_1$—H), 6.28 (2H, singlet, —OCH$_2$O—), 7.20 (1H, singlet, $C_9$—H), 7.71 (1H, singlet, $C_6$—H).

EXAMPLE 12

Pivaloyloxymethyl 7,8-methylenedioxy-5-oxo-1,2-dihydro-5H-thiazolo(3,2-a)-quinoline-4-carboxylate 7,8-Methylenedioxy-5-oxo-1,2-dihydro-5H-thiazolo(3,2-a)-quinoline-4-carboxylic acid (200 mg, 0.687 mmol) was dissolved in 5 ml of dimethyl formaide, then 152 mg of anhydrous potassium carbonate (1.1 mmol) and 328 mg (2.18 mmol) of pivaloyloxymethyl chloride were added thereto, the mixture was heated with stirring at 100° C. for six hours, the content was concentrated under reduced pressure, water was added to the residue, then insoluble matter was collected by filtration, washed with water, air dried and recrystallized from a mixture of chloroform and ether to give 200 mg of the title compound (71.9 percent yield). Melting point 229.0° to 229.5° C. Elementary analysis calculated as $C_{19}H_{19}NO_7S.\frac{1}{4}$ $H_2O$: C 55.67, H 4.79, N 3.42; Found: C 55.65, H 4.59, N 3.49.

Infrared absorption spectra (KBr, cm$^{-1}$): 1740, 1685, 1600, 1120.

Nuclear magnetic resonance spectra $\delta(CF_3CO_2D)$: 1.33 (9H, singlet, —C(CH$_3$)$_3$), 3.76 (2H, triplet, $C_2$—H), 5.70 (2H, triplet, $C_1$—H), 6.16 (2H, singlet, —COOCH$_2$OCO—), 6.20 (2H, singlet, —OCH$_2$O—), 7.12 (1H, singlet, $C_9$—H), 7.68 (1H, singlet, $C_6$—H).

EXAMPLE 13

8-Chloro-9-fluoro-5-oxo-1,2-dihydro-5H-thiazolo(3,2-a)-quinoline-4-carboxylic acid Diethyl 3-(3-chloro-2-fluorophenyl)-1,3-thiazlidin-2-ylidene malonate (7.0 grams, 0.0187 mol) was heated with stirring for two hours in 70 grams of polyphosphoric acid at 90° C. After cooled, the content was poured over into ice water, extracted with chloroform, washed with water, dried and concentrated to give 5.9 grams of oily product. This was recrystallized from ethyl acetate to give 5.05 grams (82.4 percent) of ethyl 8-chloro-9-fluoro-5-oxo-1,2-dihydro-5H-thiazolo(3,2-a)-quinoline-4-carboxylate, melting point 216° C. Elementary analysis calculated as $C_{14}H_{11}ClFNO_3S$: C 51.30, H 3.38, N 4.27; Found: C 51.31, H 3.28, N 4.06.

Infrared absorption spectra (KBr, cm$^{-1}$): 1665, 1625, 1590, 1180.

Nuclear magnetic resonance spectra $\delta(CF_3CO_2D)$: 1.60 (3H, triplet, —CH$_2$CH$_3$), 3.81 (2H, triplet, $C_2$—H), 4.29 (2H, quartet, —CH$_2$CH$_3$), 5.3 to 5.7 (2H, multiplet, $C_1$—H), 7.75 (1H, doublet, doublet, $C_7$—H), 8.27 (1H, doublet, doublet, $C_6$—H).

Then the above resulting compound (5.9 grams, 0.018 mol) was suspended in a mixture of 12.0 grams of sodium hydroxide, 100 ml of ethanol and 100 ml of water and the whole mixture was heated to reflux for two hours. After cooled, it was acidified with acetic acid and the crystals separated out were collected by filtration, washed with water, and air dried and finally recrystallized from dimethyl formamide to give 3.9 grams (72.4 percent) of the title compound, melting point 293° to 296° C. (decomposition). Elementary analysis calculated as $C_{12}H_7ClFNO_3$ S: C 48.09, H 2.35, N 4.67; Found: C 48.18, H 2.34, N. 4.56.

Infrared absorption spectra (KBr, cm$^{-1}$): 1640, 1550, 1500, 1250.

Nuclear magnetic resonance spectra $\delta(CF_3CO_2D)$: 3.83 (2H, triplet, $C_2$—H), 5.3–5.7 (2H, multiplet, $C_1$—H), 7.80 (1H, doublet, doublet, $C_7$—H), 8.32 (1H, doublet, doublet, $C_6$—H).

EXAMPLE 14

9-Fluoro-8-(4-methyl-1-piperazinyl)-5-oxo-1,2-dihydro-5H-thiazolo(3,2-a)-quinoline-4-carboxylic acid 8-Chloro-9-fluoro-5oxo-1,2-dihydro-5H-thiazolo(3,2-a)-quinoline-4-carboxylic acid (0.8 gram, 2.7 mmol) was dissolved in 5 ml of pyridine, then 2.7 grams (27 mmol) of N-methylpiperazine was added thereto, and the mixture was heated to reflux for forty eight hours. The content was concentrated under reduced pressure, water was added to the residue, and the insoluble matter was collected by filtration, washed with water, dried and recrystallized from dimethyl formamide to give 324 mg (42.0 percent) of the title compound, melting point 265° to 266° C. (decomposition). Elementary analyisis calculated as $C_{17}H_{18}FN_3O_3S$: C 56.19, H 4.99, N 11.56; Found: C 56.23, H 4.96, N 11.56.

Infrared absorption spectra (KBr, cm$^{-1}$): 1700, 1615, 1580, 1495, 1255.

Nuclear magnetic resonance spectra δ(CF$_3$CO$_2$D): 3.16 (3H, singlet, N—CH$_3$), 3.20 to 4.40 (10H, multiplet,

C$_2$—H), 5.45 (2H, triplet, C$_1$—H), 7.41 (1H, doublet, doublet, C$_7$—H), 8.30 (1H, doublet, doublet, C$_6$—H).

EXAMPLE 15

Ethyl 6-chloro-7-fluoro-5-oxo-1,2-dihydro-5H-thiazolo(3,2-a)-quinoline-4-carboxylate and Ethyl 8-chloro-7-fluoro-5-oxo-1,2-dihydro-5H-thiazolo(3,2-a)-quinoline-4-carboxylate Diethyl 3-(3-chloro-4-fluorophenyl)-1,3-thiazolidin-2-ylidene malonate (7.15 grams, 0.019 mol) was added to 71 grams of polyphosphoric acid and the mixture was heated with stirring in an oil bath at 120° C. for two hours. After the reaction was completed, the mixture was poured over into ice water with ice cooling. After the mixture was stirred for a while, crystals separated out were collected by filtration and 5.08 grams of beige powder. The powder was separated by purification using chloroform as a developer in dry column to give the title compounds.

Physical properties and instrumental data for the 6-chloro-7-fluoro compound are as follows: Yield 2.97 grams (58.5 percent), melting point 278° C.

Infrared absorption spectra (KBr, cm$^{-1}$): 1710, 1680, 1620.

Elementary analysis calculated as C$_{14}$H$_{11}$FClNO$_3$S: C 51.30, H 3.38, N 4.27; Found: C 51.38, H 3.25, N 4.11.

Nuclear magnetic resonance spectra δ(CF$_3$CO$_2$D): 1.63 (3H, triplet, —CH$_3$), 3.85 (2H, multiplet, C$_2$—H), 4.78 (2H, quartet, —OCH$_2$—), 5.28 (2H, multiplet, C$_1$—H), 7.81 (1H, singlet, C$_9$—H), 7.91 (1H, doublet, C$_8$—H).

Physical properties and instrumental data for the 8-chloro-7-fluoro compound are as follows: Pale yellow powdery crystals. Yield 2.04 grams (40.2 percent), melting point 266° C.

Infrared absorption spectra (KBr, cm$^{-1}$): 1750, 1680, 1590.

Elementary analysis calculated as C$_{14}$H$_{11}$FClNO$_3$S.¼H$_2$O): C 50.61, H 3.49, N 4.22; Found: C 50.69, H 3.24, N 4.07.

Nuclear magnetic resonance spectra δ(CF$_3$CO$_2$D): 1.65 (3H, triplet, —CH$_3$), 3.28 (2H, triplet, C$_2$—H), 4.75 (2H, quartet, —CH$_2$—), 5.23 (2H, triplet, C$_1$—H), 7.50-8.20 (2H, multiplet, aromatic ring—H).

EXAMPLE 16

6-Chloro-7-fluoro-5-oxo-1,2-dihydro-5H-thiazolo(3,2-a)quinoline-4-carboxylic acid One gram (3.05 mmol) of ethyl 6-chloro-7-fluoro-5-oxo-1,2-dihydro-5H-thiazolo(3,2-a)-quinoline-4-carboxylate was added to 50 ml of a mixture of ethanol and water (1:1), then 3 ml of 2 N sodium hydroxide solution was added thereto, and the mixture was heated to reflux for two hours. When the reaction was completed, the mixture was cooled to a room temperature and crystals separated out were collected by filtration to give 700 mg of sodium salt. The resulting sodium salt was suspended in water at hot state and dimethyl formamide was added thereto to prepare uniform solution. The solution was adjusted to pH≈7.0 usng 1 N aqueous solution of acetic acid, crystals separated out were collected by filtration, washed with acetone and ether, ari dried and the title compound was obtained. White powder. Yield 629 mg (68.8 percent). Melting point 326° C. (decomposition). Elementary analysis calculated as C$_{12}$H$_7$FClNO$_3$S: C 48.09, H 2.35, N 4.67, Found: C 48.28, H 2.15, N 4.44.

Infrared absorption spectra (KBr, cm$^{-1}$): 1690, 1595.

Nuclear magnetic resonance spectra δ(CF$_3$CO$_2$D): 3.85 (2H, triplet, C$_2$—H), 5.27 (2H, triplet, C$_1$—H), 7.6-8.0 (2H, multiplet, aromatic ring—H).

EXAMPLE 17

7-Fluoro-6-(1-piperazinyl)-5-oxo-1,2-dihydro-5H-thiazolo(3,2-a)quinoline-4-carboxylic acid 6-Chloro-7-fluoro-1,2-dihydro-5-oxo-5H-thiazolo(3,2-a) quinoline 4-carboxylic acid (410 mg, 1.3 mmol) and 1.3 grams (15 mmol) were added to 20 ml of pyridine and the mixture was heated to reflux for nine hours. When the reaction was completed, the mixture was allowed to cool to a room temperature, separated crystals were collected by filtration, washed with small amounts of acetone and ether, and air dried to give the title compound. Yellow powders. Yield 445 mg (93.7 percent). Melting point 249° C. (decomposition). Elementary analysis calculated as C$_{16}$H$_{16}$FN$_3$O$_3$S.H$_2$O: C 51.06, H 4.82, N 11.16; Found: C 51.00, H 4.94, N 11.26

Infrared absorption spectra (KBr, cm$^{-1}$): 3000-2400, 1600.

Nuclear magnetic resonance spectra δ(CF$_3$CO$_2$D): 3.50-5.50 (12H, multiplet, C$_1$—H, C$_2$—H,

7.80-8.30 (2H, multiplet, aromatic ring—H)

EXAMPLE 18

8-Chloro-7-fluoro-5-oxo-1,2-dihydro-5H-thiazolo(3,2-a)-quinoline-4-carboxylic acid Six hundred mg (1.83 mmol) of ethyl 8-chloro-7-fluoro-5-oxo-1,2-dihydro-5H-thiazolo(3,2-a)-quinoline-4-carboxylate obtained in Example 15 was added to a mixed solvent of ethanol and water (1:1), then 2 ml of 2 N aqueous solution of sodium hydroxide was added thereto, and the mixture was heated to reflux for two hours. When the reaction was completed, ethanol was evaporated therefrom, the residual aqueous solution was adjusted to pH nearly 7.0 with 1 N aqueous solution of acetic acid and, after stirring for a while, crystals separated out therefrom were collected by filtration, successively washed with ethanol, acetone and ether and air dried to give 501 mg (91.4 percent) of the title compound, melting point 318° C. (decomposition). Elementary analysis calculated as C$_{12}$H$_7$FClNO$_3$S: C 48.09, H 2.35, N. 4.67; Found: C 48.28, H 2.14, N 4.37.

Infrared absorption spectra (KBr, cm$^{-1}$): 1700, 1590.

Nuclear magnetic resonance spectra δ(CF$_3$CO$_2$D): 3.82 (2H, triplet, C$_2$—H), 5.23 (2H, triplet, C$_1$—H), 8.00 (1H, doublet, C$_9$—H), 8.23 (1H, doublet, C$_6$—H).

EXAMPLE 19

7-Fluoro-8-(4-methyl-1-piperazinyl)-5-oxo-1,2-dihydro-5H-thiazolo(3,2-a)-quinoline-4-carboxylic acid A mixture of 1 gram (3.3 mmol) of 8-chloro-7-fluoro-5-oxo-1,2-dihydro-5H-thiazolo(3,2-a)-quinoline-4-carboxylic acid, 1.65 g. (0.0165 mol) of N-methylpiperazine and 20 ml of pyridine was heated to reflux. After twelve hours, 1.65 g. (0.0165 mol) of N-methylpiperazine was added thereto again and the heating to reflux was continued for twelve hours. When the reaction was completed, the mixture was allowed to cool to a room temperature, crystals separated out therefrom were collected by filtration, washed with pyridine and ether and air dried to give the title compound. Yellow powdery crystals. Yield 720 mg (60 percent).

Melting point 265° C. (decomposition). Elementary analysis calculated as C$_{17}$H$_{18}$FN$_3$O$_3$S: C 56.19, H 4.99, N 11.56; Found: C 56.19, H 4.97, N 11.61.

Both infrared absorption spectra and nuclear magnetic resonance spectra concided with those of the Example 7.

EXAMPLE 20

7-Fluoro-8-(1-piperazinyl)-5-oxo-1,2-dihydro-5H-thiazolo(3,2-a)quinoline-4-carboxylic acid To one gram of 8-chloro-7-fluoro-5-oxo-1,2-dihydro-5H-thiazolo(3,2-a)quinoline-4-carboxylic acid (33 mmol) were added 2.87 grams (33 mmol) of anhydrous piperazine and 30 ml of pyridine and the resulting suspension was heated to reflux for twelve hours in an oil bath. Pyridine was evaporated therefrom under reduced pressure, water was added to the residue, and the mixture was again concentrated under reduced pressure. Water was added to the resulting residue, then 4 ml of 2 N aqueous solution of sodium hydroxide was added thereto, and the mixture was warmed to prepared uniform solution. Then this was adjusted to pH nearly seven with 1 N hydrochloric acid. Crystals separated out therefrom were collected by filtration, washed with water, washed with acetone and ether, and air dried to give the title product as powdery crystals. Yield 997.8 mg (90.7 percent). Melting point 287° to 288° C. (decomposition). Elementary analysis calculated as C$_{16}$H$_{16}$FN$_3$O$_3$S.3H$_2$O: C 47.64, H 5.50, N 10.41; Found: C 47.60, H 5.42, N 10.63.

Infrared absorption spectra (KBr, cm$^{-1}$): 3000–2400, 1600, 1565.

Nuclear magnetic resonance δ(CF$_3$CO$_2$D): 3.82 (10H, multiplet, C$_2$—H,

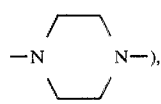

5.15 (2H, multiplet, C$_1$—H), 7.15 (1H, doublet, C$_9$—H), 8.11 (1H, doublet, C$_6$—H).

EXAMPLE 21

7-Fluoro-8-(4-phthalidyl-1-piperazinyl)-5-oxo-1,2-dihydro-5H-thiazolo(3,2-a)-quinoline-4-carboxylic acid A mixture of 300 mg (0.9 mmol) of 7-fluoro-8-(1-piperazinyl)-5-oxo-1,2-dihydro-5H-thiazolo(3,2-a)-quinoline-4-carboxylic acid and 13.5 mg (0.9 mmol) of o-phthal aldehyde acid was suspended in 4 ml of dimethyl formamide and the whole mixture was heated with stirring at 120° C. for seven hours in an oil bath. When the reaction was completed, the mixture was allowed to cool to room temperature and, by collecting the crystals separated out therefrom by filtration, the title compound was obtained as powder. Yield 207 mg (47.7 percent). Melting point 261° to 262° C. (decomposition). Elementary analysis calculated as C$_{24}$H$_{20}$FN$_3$O$_5$S: C 59.87, H 4.19, N 8.73; Found: C 60.09, H 4.32, N 8.64.

Infrared absorption spectra (KBr, cm$^{-1}$): 1750, 1690, 1600.

Nuclear magnetic resonance δ(CF$_3$CO$_2$D): 3.50–4.80 (10H, multiplet, C$_2$—H,

4.88–5.40 (2H, multiplet, C$_1$—H), 7.00–7.35 (1H, multiplet, C$_9$—H), 7.40–8.60 (4H, multiplet, aromatic ring), 8.15 (1H, doublet, C$_6$—H), 9.70 (1H, wide singlet,

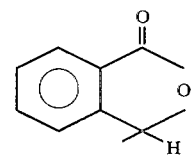

EXAMPLE 22

7-Fluoro-8-(4-(2-hydroxy-3-methoxy-1-propyl)-1-piperazinyl)-5-oxo-1,2-dihydro-5H-thiazolo(3,2-a)-quinoline-4-carboxylic acid A mixture of 500 mg (1.67 mmol) of 8-chloro-7-fluoro-5-oxo-1,2-dihydro-5H-thiazolo(3,2-a)-quinoline-4-carboxylic acid and 1.45 grams (8.3 mmol) of N-(2-hydroxy-3-methoxy-1-propyl)-piperazine was suspended in 20 ml of pyridine and the mixture was heated to reflux for thirty six hours. When the reaction was completed, pyridine was evaporated therefrom under reduced pressure and ethanol was added to the residue. Insoluble matters were filtered, washed with ether, and recrystallized from acetonitrile to give the title compound as flaky crystals. Yield 397.8 mg (54.5 percent). Melting point 224° C. Elementary analysis calculated as C$_{20}$H$_{24}$FN$_3$O$_5$S: C 54.91, H 5.53, N 9.60; Found: C 54.94, H 5.55, N 9.60.

Infrared absorption spectra (KBr, cm$^{-1}$): 2830, 1695, 1630, 1590.

Nuclear magnetic resonance spectra δ(CF$_3$CO$_2$D): 3.60 (3H, singlet, N—CH$_3$), 3.20–4.90 (18H, multiplet,

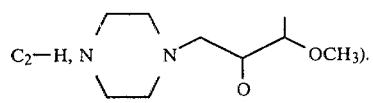

7.15 (1H, doublet, C$_9$—H), 8.12 (1H, doublet, C$_6$—H).

EXAMPLE 23

7-Fluoro-8-(4-(2-hydroxyethyl)-1-piperazinyl)-5-oxo-1,2-dihydro-5H-thiazolo-(3,2-a)-quinoline-4-carboxylic acid A mixture of 500 mg (1.67 mmol) of 8-chloro-7-fluoro-5-oxo-1,2-dihydro-5H-thiazolo(3,2-a)-quinoline-4-carboxylic acid and 1.09 grams (8.34 mmol) of N-(beta-hydroxyethyl)-piperidine was suspended in 20 ml of pyridine and the mixture was heated to reflux for thirty two hours. When the reaction was completed, the mixture was cooled to a room temperature, crystals separated out therefrom were collected by filtration, successively washed with pyridine, ethanol and ether, and recrystallized from dimethyl formamide to give the title compound as pale yellow powders. Yield 426.6 mg (65 percent). Melting point 256° to 256.5° C. Elementary analysis calculated as $C_{18}H_{20}FN_3O_4S$: C 54.95, H 5.12, N 10.68; Found: C 54.52, H 5.14, N 10.73.

Infrared absorption spectra (KBr, cm$^{-1}$): 1695, 1625, 1590.

Nuclear magnetic resonance spectra $\delta(CF_3CO_2D)$: 3.20–4.70 (14H, multiplet, $C_2$—H,

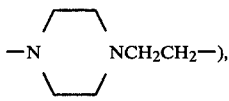

5.18 (2H, multiplet, $C_1$—H), 7.17 (1H, doublet, $C_9$—H), 8.12 (1H, doublet, $C_6$—H).

EXAMPLE 24

8-Chloro-7-fluoro-5-oxo-1,2-dihydro-5H-thiazolo(3,2-a)-quinoline-4-carboxylic acid ethyl ester (a) To ten grams (0.029 mol) of diethyl (3-chloro-5-fluorophenyl)-aminomercaptomethylene-malonate were added 20 ml of acetonitrile and 6.0 grams (0.043 mol) of anhydrous potassium carbonate, then 4.5 grams (0.029 mol) of p-methoxybenzyl chloride was dropped thereinto during about ten minutes at room temperature with stirring and, when the dropping was completed, the mixture was stirred at room temperature for three hours. Anhydrous potassium carbonate was filtered out and washed with a small amount of acetonitrile. Washings were combined, acetonitrile was evaporated therefrom under reduced pressure, the residue was dissolved in ethyl acetate, the solution was washed with water, and dried on magnesium sulfate.

Ethyl acetate was evaporated therefrom to give 14.0 grams of yellow oil. The yellow oil was subjected to a column chromatography on silica gel (Wakogel C-300) and eluted with benzene to give diethyl (3-chloro-4-fluorophenyl)amino(4-methoxybenzyl)-thiomethylenemalonate. Pale yellow oil. Yield 10.9 grams (81 percent). Elementary analysis calculated as $C_{22}H_{23}ClFNO_5S$: C 56.47, H 4.95, N 2.99; Found: C 56.71, H 5.06, N 3.00.

Infrared absorption spectra (liquid memebrane, cm$^{-1}$): 1730, 1660, 1610, 1510

Nuclear magnetic resonance $\delta(CDCl_3)$: 1.27 (6H, triplet, $CO_2CH_2\underline{CH}_3\times 2$), 3.60 (2H, singlet, S—$CH_2$—), 3.72 (3H, singlet, $OCH_3$), 4.18 (4H, quartet, $O\underline{CH}_2CH_3\times 2$) 6.58–7.45 (7H, multiplet, aromatic ring-H), 10.45 (1H, wide singlet, N$\underline{H}$), vanished when $D_2O$ was added thereto.

(b) To 7.2 grams (0.0154 mol) of diethyl (3-chloro-4-fluorophenyl) amino-(4-methoxybenzyl)-thiomethylenemalonate was added 14.4 grams of biphenyl ether and the mixture was heated with stirring for three minutes at 250° C. After it was cooled to a room temperature, 30 ml of n-hexane was added thereto so that crystals were appeared. The crystals were collected by filtration, washed with n-hexane and recrystallized from isopropyl ether to give ethyl 7-chloro-6-fluoro-2-(4-methoxybenzylthio)-4-oxo-1,4-dihydroquinoline-3-carboxylate. Yield 4.3 grams (66 percent). Melting point 142° C. Elementary analysis calculated as $C_{20}H_{17}ClFNO_4S$: C 56.94, H 4.06, N 3.32; Found: C 56.98, H 4.26, N 3.68

Infrared absorption spectra (KBr, cm$^{-1}$): 1655, 1626, 1592, 1556.

Nuclear magnetic resonance spectra $\delta(CDCl_3)$: 1.45 (3H, triplet, $OCH_2\underline{CH}_3$), 3.74 (3H, singlet, $O\underline{CH}_3$), 4.38 (2H, singlet, $S\underline{CH}_2$), 4.45 (2H, quartet, $O\underline{CH}_2CH_3$), 6.75, 7.32 (4H, doublet, doublet, aromatic ring), 7.75 (1H, doublet, $C_5$—H), 7.78 (1H, singlet, $C_8$—H), 13.17 (1H, wide singlet, N$\underline{H}$), disappeared by addition of $D_2O$.

(c) To 1.7 ml (0.01896mol) of trifluoromethane sulfonic acid were added 2.06 mol (0.0189 mol) of anisole and 8.8 ml (0.11378 mol) of trifluoroacetic acid and the mixture was cooled at 0° C. in an ice-sodium chloride bath. With stirring, 2.0 grams (0.0047 mol) of ethyl 7-chloro-6-fluoro-2-(4-methoxybenzylthio)-4-oxo-dihydroquinoline-3-carboxylate was added thereto and the mixture was stirred for about twenty minutes. Then trifluoroacetic acid and anisole were evaporated therefrom under reduced pressure and 15 grams of ice water was added to the residue. Yellow crystals appeared immediately. The crystals were collected by filtration, washed with water, dried, and recrystallized from dimethyl formamide and ether to give ethyl 7-chloro-6-fluoro-2-mercapto-4-oxo-1,4-dihydroquinoline-3-carboxylate. Yellow crystals. Yield 1.4 grams (98 percent). Melting point 221° to 223° C. (decomposition). Elementary analysis calculated as $C_{12}H_{19}ClFNO_3S$: C 47.-7, H 3.01, N 4.64; Found: C 47.81, H 3.25, N 4.81.

Infrared absorption spectra (KBr, cm$^{-1}$): 3100, 2700–1940, 1643, 1615, 1590.

Nuclear magnetic resonance spectra $\delta(DMF-d_6)$: 1.28 (3H, triplet, $OCH_2\underline{CH}_3$), 4.25 (2H, quartet, $O\underline{CH}_2CH_3$), 7.66 (1H, doublet, $C_8$-H), 7.89 (1H, doublet, $C_5$—H), 13.15 (1H, wide singlet) disappeared by addition of $D_2O$.

(d) Three grams (0.01 mol) of ethyl 7-chloro-6-fluoro-2-mercapto-4-oxo-1,4-dihydroquinoline-3-carboxylate was dissolved in 10 ml of dimethyl formamide, then 4.1 grams (0.03 mol) of anhydrous potassium carbonate was added thereto and, with stirring at a room temperature, 1.9 grams (0.01 mol) of ethylene dibromide was dropped thereinto. The mixture was stirred at a room temperature overnight. The content was concentrated under reduced pressure and water was added to the residue. Crystals separated out therefrom were collected by filtration immediately, washed with water, dried and the crystals were recrystallized from ethanol to give the title compound. Colorless crystals. Yield 3.5 grams (94 percent). All of melting point, elementary analysis data, infrared absorption spectra, and nuclear magnetic resonance spectra coincided with those in example 15.

EXAMPLE 25

Ethyl 6-chloro-7-fluoro-5-oxo-1,2-dihydro-5H-thiazolo(3,2-a)-quinoline-4-carboxylate and ethyl 8-chloro-7-fluoro-5-oxo-1,2-dihydro-5H-thiazolo(3,2-a)-quinoline-4-carboxylate (a) Two hundred and thirty one mg (0.53 mmol) of diethyl (2-acetoxyethyl)thio-(3-chloro-4-fluorophenyl)-aminomethylenemalonate was dissolved in 0.5 ml of diphenyl ether and the mixture was heated with stirring at 250° C. for five minutes. After cooled, insoluble matters were collected by filtration, washed with ether and air dried to give 82 mg of pale yellow powders. The powders were subjected to separation and purification by a silica gel column chromatography to give 12 mg (6.6 percent) of ethyl 6-chloro-7-fluoro-5-oxo-1,2-dihydro-5H-thiazolo(3,2-a)-quinoline-4-carboxylate and 48 mg (26.2 percent) of ethyl 8-chloro-7-fluoro-5-oxo-1,2-dihydro-5H-thiazolo(3,2-a)-quinoline-4-carboxylate.

(b) Diethyl (3-chloro-4-fluorophenyl)amino-(2-trimethylsilyloxyethyl)-thiomethylenemalonate (173 mg, 0.37 mmol) was dissolved in 0.4 ml of diphenyl ether and the solution was heated with stirring at 250° C. for five minutes. After cooled, insoluble matters were collected by filtration, washed with ether and air dried to give 93 mg of pale yellow powders. The powders were subjected separation and purification by a silica gel column chromatography to give 9 mg (7.0 percent) of ethyl 6-chloro-7-fluoro-5-oxo-1,2-dihydro-5H-thiazolo(3,2-a)-quinoline-4-carboxylate and 76 mg (59.3 percent) of ethyl 8-chloro-7-fluoro-5-oxo-1,2-dihydro-5H-thiazolo(3,2-a)-quinoline-4-carboxylate.

(c) Two hundred and thirty eight mg (0.5 mmol) of diethyl (3-chloro-4-fluorophenyl)-amino-(2-(2-tetrahydropyranyloxy)ethyl)-thiomethylene malonate was dissolved in 0.6 ml of diphenyl ether and the solution was heated with stirring at 250° C. for five minutes. After cooled, the insoluble matters appeared were collected by filtration, washed with ether, and air dried to give 65 mg of yellow powder. The powder was subjected to separation and purification by a silica gel column chromatography to give 7 mg (4.0 percent) of ethyl 6-chloro-7-fluoro-5-oxo-1,2-dihydro-5H-thiazolo(3,2-a)-quinoline-4-carboxylate and 43 mg (25.0 percent) of ethyl 8-chloro-7-fluoro-5-oxo-1,2-dihydro-5H-thiazolo-(3,2-a) quinoline-4-carboxylate.

Physical constants of the above compounds were identical with those in compounds of Example 15.

The compounds of the invention are used to treat bacterial and fungal infections in mammals by administering to the sufferer an anti-bacterial or anti-fungal amount of the compound of the invention, preferably in the form of a pharmaceutical composition comprising an anti-bacterial or anti-fungal amount of the compound in combination with a pharmaceutically acceptable, nontoxic, inert diluent or carrier, the carrier comprising one or more solid, semi-solid or liquid diluent, filler and formulation adjuvant which is nontoxic, inert an pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses, or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage will be from 0.1 to 150 mg of the compound of the present invention, preferably 5 to 20 mg, per kg of body weight per day. In some instances, a sufficient therapeutic effect can be obtained at a lower dose, while in others a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and, optionally, with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free-flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous solution, while elixirs are prepared through the use of nontoxic alcoholic vehicles. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccarin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as aqueous or deaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories, in which the compound is admixed with lowmelting, water-soluble or insoluble solids such as polyethylene glycol, cocoa butter, higher esters as for example myristyl palmitate, or mixtures thereof.

While the routes of administration of the compound of the invention include oral, parenteral (i.e., intramuscular, intraperitoneal and intravenous), and rectal, oral administration is particularly preferred.

The preferred pharmaceutical compositions are therefore those in a form suitable for oral administration, such as tablets and liquids.

What is claimed:

1. A compound of the formula

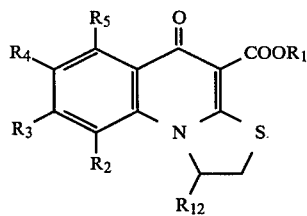

in which:

$R_1$ is hydrogen, alkali metal, alkali earth metal, lower alkyl or pivaloyloxymethyl;

$R_2$ is hydrogen or halogen;

$R_3$ is hydrogen, halogen or piperazinyl unsubstituted or substituted by lower alkyl, (hydroxy)lower alkyl, (lower alkoxy)(hydroxy)lower alkyl, or phthalidyl;

$R_4$ is hydrogen, halogen or lower alkoxy; or $R_3$ and $R_4$ together with the carbon atoms to which they are attached form a 5, 6 or 7-membered ring containing carbon atoms and 1 or 2 oxygen atoms;

$R_5$ is hydrogen, halogen or piperazinyl unsubstituted or substituted by lower alkyl, hydroxy(lower alkyl) or (lower alkoxy)(hydroxy) lower alkyl, or phthalidyl; and $R_{12}$ is hydrogen or lower alkyl; provided that at least one of $R_3$ and $R_5$ is said unsubstituted or substituted piperazinyl, and pharmaceutically acceptable acid addition salts thereof.

2. The compound according to claim 1, wherein $R_3$ and $R_4$ together represent methylenedioxy and form a five membered ring with the carbon atoms to which they are attached.

3. The compound according to claim 1, wherein said lower alkyl and lower alkoxy are of 1 to 4 carbon atoms.

4. The compound, which is 7-fluoro-8-(4-methyl-1-piperazinyl)-5-oxo-1,2-dihydro-5H-thiazolo(3,2-a)-quinoline-4-carboxylate acid.

5. A pharmaceutical composition for treatment of bacterial and fungal infections which comprises an anti-bacterial or anti-fungal effective amount of the compound according to claim 1 in combination with a pharmaceutically acceptable carrier or diluent therefor.

6. A method of treatment of bacterial or fungal infections im mammals, which comprises administering to the sufferer an anti-bacterial or anti-fungal effective amount of the compound according to claim 1.

7. The compound according to claim 1, which is 7-Chloro-6-(1-piperazinyl)-5-oxo-1,2-dihydro-5H-thiazolo[3,2-a]-quinoline-4-carboxylic acid.

8. The compound according to claim 1, which is 7-Fluoro-1-methyl-8-(4-methyl-1-piperazinyl)-5-oxo-1,2-dihydro-5H-thiazolo(3,2-a)-quinoline-4-carboxylic acid.

9. The compound according to claim 1, which is 9-Fluoro-8-(4-methyl-1-piperazinyl)-5-oxo-1,2-dihydro-5H-thiazolo (3,2-a)-quinoline-4-carboxylic acid.

10. The compound according to claim 1, which is 7-Fluoro-6-(1-piperazinyl)-5-oxo-1,2-dihydro-5H-thiazolo(3,2-a) quinoline-4-carboxylic acid.

11. The compound according to claim 1, which is 7-Fluoro-8-(1-piperazinyl)-5-oxo-1,2-dihydro-5H-thiazolo(3,2-a) quinoline-4-carboxylic acid.

12. The compound according to claim 1, which is 7-Fluoro-B  8-(4-phthalidyl-1-piperazinyl)-5-oxo-1,2-dihydro-5H-thiazolo(3,2-a)-quinoline-4-carboxylic acid.

13. The compound according to claim 1 which is 7-Fluoro-8-(4-(2-hydroxy-3-methoxy-1-propyl)-1-piperazinyl)-5-oxo-1,2-dihydro-5H-thiazolo(3,2-a)-quinoline-4-carboxylic acid.

14. The compound according to claim 1 which is 7-Fluoro-8-(4-(2-hydroxyethyl)-1-piperazinyl)-5-oxo-1,2-dihydro-5H-thiazolo-(3,2-a)-quinoline-4-carboxylic acid.

* * * * *